United States Patent [19]

Shenoy

[11] 4,061,745
[45] Dec. 6, 1977

[54] AZETO [2,3-b][1,4] BENZO DIAZEPINES

[75] Inventor: Umakant Devdas Shenoy, London, England

[73] Assignee: DDSA Pharmaceuticals Ltd., London, England

[21] Appl. No.: 576,921

[22] Filed: May 12, 1975

[30] Foreign Application Priority Data

May 14, 1974 United Kingdom ............... 21195/74

[51] Int. Cl.$^2$ .................... C07D 487/04; A61K 31/55
[52] U.S. Cl. ............................. 424/244; 260/239 A; 260/239 BD
[58] Field of Search .................... 260/239 A; 424/244

[56] References Cited

PUBLICATIONS

Reinhoudt et al., Chem. Abs. 78, 136248e (1973).

*Primary Examiner*—Alton D. Rollins
*Assistant Examiner*—Mark L. Berch
*Attorney, Agent, or Firm*—Burgess, Dinklage & Sprung

[57] ABSTRACT

Novel aldehyde adducts of 1,4-benzodiazepines-4-oxides, novel azeto-[1,4]-benzodiazepine derivatives derived therefrom, acid addition salts thereof and methods for their preparation. The aldehyde adducts have the general formula I; the azeto-[1,4]-benzodiazepine derivatives have the general formula III.

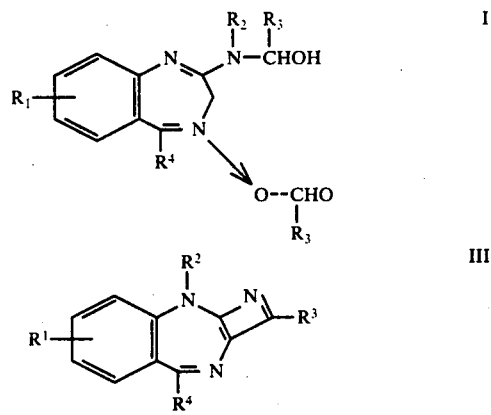

8 Claims, 6 Drawing Figures

AZETO [2,3,-b][1,4] BENZO DIAZEPINES

BACKGROUND OF THE INVENTION

The novel 1,4-benzodiazepine-4-oxide aldehyde adducts of the invention are aldehyde adducts of benzodiazepines unsaturated at the 1 position, referred to as 3H-1,4-benzodiazepines. 3H-1,4-benzodiazepines are known, and are useful as sedatives and tranquillizers in the field of human therapy. The azeto-[1,4]-benzodiazepine ring structure is an entirely new heterocyclic ring structure.

SUMMARY OF THE INVENTION

It is an object of the invention to provide novel aldehyde adducts of 1,4-benzodiazepin-4-oxides which are useful in the fields of human and animal therapy and as intermediates in the preparation of other useful compounds.

It is also an object of the invention to provide novel azeto-[1,4]-benzodiazepine compounds which are themselves useful in both of the above fields of therapy.

The novel aldehyde adducts of 1,4-benzodiazepine-4-oxides of the invention have the general formula I in which the symbols are as defined below. The parent 1,4-benzodiazepine-4-oxides have the general formula II in which the symbols are as defined below. The novel azeto-[1,4]-benzodiazepines of the invention have the general formula III in which the symbols are as defined below.

In the above formulae I to III:

$R_1$ represents a hydrogen or halogen atom or a trifluoromethyl, cyano, nitro, lower alkyl, lower alkoxy or lower alkylthio group;

$R_2$ represents a lower alkyl, hydroxy-(lower alkyl), lower alkenyl or benzyl group;

$R_3$ represents a lower alkyl group; and $R_4$ represents a phenyl, (lower alkyl)-phenyl, nitrophenyl, halophenyl or pyridyl group.

As used herein, the term "halogen" means bromine, chlorine, fluorine, or iodine. The term "lower alkyl" refers to both straight-chain and branched-chain alkyl groups containing from 1 to 10 carbon atoms, for example, methyl, ethyl, n-propyl, iso-propyl, n-butyl, n-amyl and n-hexyl. The term "lower alkenyl" means both straight-chain and branched-chain alkenyl groups containing from 2 to 6 carbon atoms, for example vinyl, allyl, butenyl, hexenyl and isobutenyl.

The compounds of the general formula I and their acid addition salts are products in which there can be identified by infrared and proton magnetic resonance spectroscopy the elements of a benzodiazepine ring and the proton magnetic resonance spectrum of which shows a shift at about $\delta = 9.7$ p.p.m assignable to the aldehydic protons.

The compounds I can be prepared according to the invention by reacting, in aqueous acid, a solution of a 1,4-benzodiazrepine-4-oxide of the general formula IV (in which the symbols are as above defined) with an excess, preferably 2 or more molar equivalents, of an aldehyde having the general formula $R_3 CHO$ in which $R_3$ is as above defined. The compound IV is preferably used in solution in aqueous hydrochloric acid, in which case the product is the hydrochloride salt, V The compound IV or its hydrochloride salt is preferably dissolved in aqueous hydrochloric acid so as to provide a molar ratio of acid: base of 2 or more. The amount of water should be sufficient to ensure that the compound remains in solution, from 300 to 500 ml of water generally being sufficient to dissolve 1 mole of compound IV.

The aldehyde $R_3$—CHO is preferably added in an amount of 2 to 6 moles, advantageously about 4 moles, per mole of compound IV. Stirring is preferably continued for up to 72 hours, generally 60 to 72 hours, at room temperature to enable the reaction to proceed sufficiently near to completion. The product generally precipitates gradually during this time. If no precipitate forms even after 72 hours, the reaction mixture may be stirred with methylene dichloride for 24 hours, during which a crystalline product is generally precipitated. If no precipitate forms even after this treatment, the methylene dichloride layer may be separated and the product precipitated by addition of an excess of diethyl ether and petroleum spirit.

The product I may be purified by filtering, washing with water, drying and recrystallizing from a suitable solvent; preferably without using any heat.

Certain suitable starting materials of the general formula IV are described and claimed in British Pat. Specification Nos. 864,824, 972,969 and 986,903.

The compounds I are of value not only by virtue of their pharmacological properties but as intermediates in the preparation of compounds II and III.

The parent compounds II can be prepared merely by crystallizing the compounds I from a boiling solvent such as isopropyl alcohol, whereupon the aldehyde dissociates from the 1,4-benzodiazepine aldehyde adduct to yield compounds II as described in British Pat. Specification No 1,359,287.

The invention also provides a method of making the compounds of the general formula III which comprises treating a compound of the general formula I with an organic or inorganic base, preferably a strong base such as sodium or potassium hydroxide. The products III are azetes with a fundamentally new stable ring structure that is of major importance from a theoretical point of view as leading the way to a large number of new syntheses. The products III also show promise as pharmocologically valuable compounds, with indications of an action on the central nervous system, as well as possible anti-inflammatory and diuretic properties.

The preparation of the azetes III may be carried out by reacting a solution or suspension of a compound I, for example in methanol, ethanol or isopropanol, with the base. The reaction is preferably allowed to continue at room temperature for several hours, during which time the product crystallizes. The product III may be isolated by filtration and washed with water until free from alkali. They may be converted into their acid addition salts according to the invention by treatment with suitable pharmacologically acceptable organic or inorganic acids, for example hydrochloric acid, hydrobromic acid, nitric acid, sulphuric acid, acetic acid, formic acid, phosphoric acid, perchloric acid, succinic acid, maleic acid, citric acid or fumaric acid. In particular, the hydrochloride salts have been found to be perfectly stable.

Both the compounds I and the compounds III show the psychotropic action on the central nervous system commonly associated with the benzodiazepine ring, giving the compounds tranquillizing, sedative and hypnotic properties. To produce a tranquillizing effect they would be administered at a dosage of from 1 mg to 10 mg depending on the age and condition of the patient. In larger doses they produce sedation, and when the sedative dose is increased they have hypnotic effects. They can be applied in the form of tablets, capsules, suppositories or syrup, or in injectable form. The invention accordingly provides therapeutic compositions comprising one or more compounds of the general formula I or III or acid addition salts thereof in admixture with a pharmacologically acceptable diluent or carrier.

The following Examples illustrate the invention but are not to be regarded as limiting it in any way.

EXAMPLE 1

To a solution of 7-chloro-2-methylamino-5-phenyl-3H-1,3-benzodiazepine-4-oxide hydrochloride (16.8 g) in water (200 ml) in a 500 ml round-bottomed flask equipped with a magnetic stirrer there was added concentrated hydrochloric acid (5.5 ml) and n-propionaldehyde (15 ml). The flask was stoppered and the reaction mixture was stirred for 72 hours. A solid was precipitated and was filtered, washed with water (2 × 25 ml), pressed well and air dried. The solid was then recrystallized from a cold mixture of methanol, ether and petroleum ether and formed colourless crystals melting at 198°–4° C with decomposition. The yield of the n-propionaldehyde adduct of 7-chloro-2-(N-methyl-1-hydroxypropylamino)-5-phenyl-3H-1,4-benzodiazepine-4-oxide hydrochloride (Compound V; $R_1$=chlorine in the 7-position, $R_2$=methyl, $R_3$=ethyl, $R_4$=phenyl) was 2.6 grams.

The results of analysis were as follows:

Calculated for $C_{22}H_{27}Cl_2N_3O_3$: C=58.4%; H=6.0%; N=9.3%; Found: C=58.6%; H=6.0%; N=9.4%.

Figure 1:
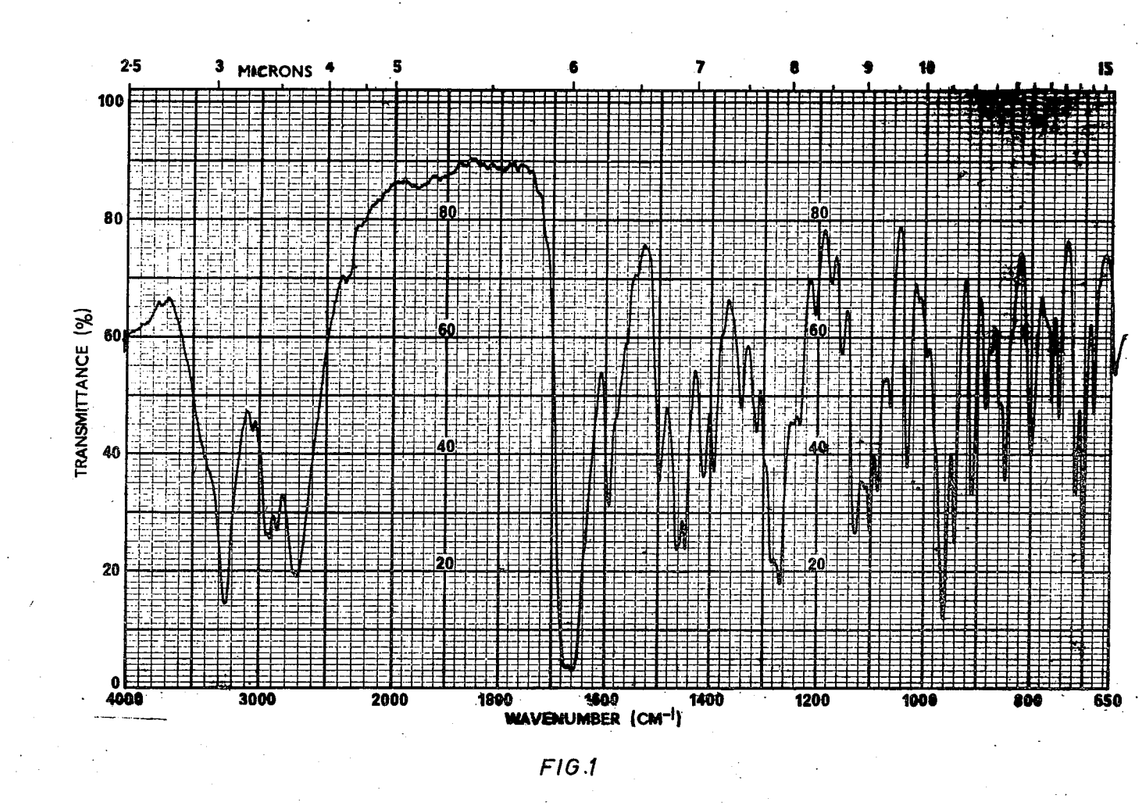
Figure 2:
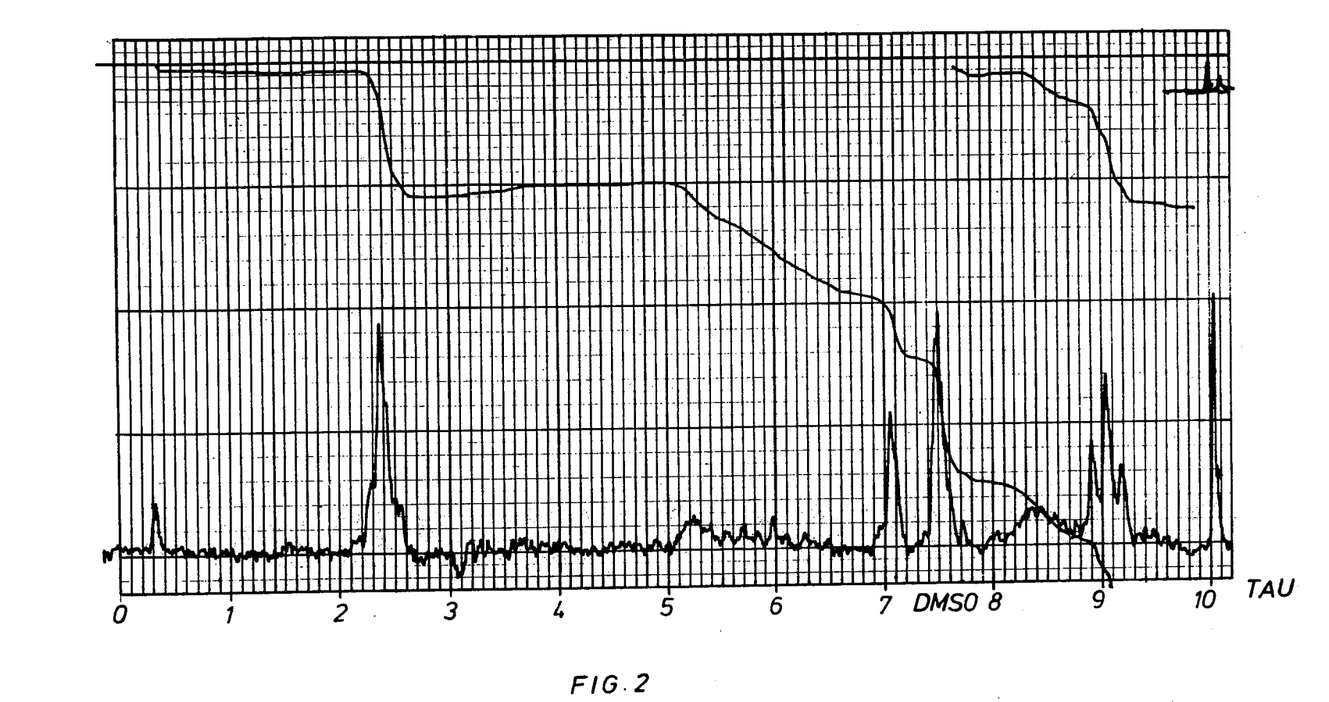

The infrared (IR) spectrum of the product is shown as FIG. 1 of the drawings, and the nuclear magnetic resonance (NMR) spectrum is shown as FIG. 2. In the NMR spectrum the following shifts can be assigned to given groups:

| $\delta$(p.p.m.) | | Assignation to: | |
|---|---|---|---|
| 1.00 (triplet) | | —$CH_3$ | |
| 1.28–1.9 | (complex multiplet) | —$CH_2$— | Two-$C_2H_5$ groups |
| 2.94 | (complex singlet) | —N—$CH_3$ | |
| 3.4–5 | (complex multiplet) | | |
| 7.3–7.9 | (complex multiplet) | aromatic protons. | |
| 9.68 | (broad singlet) | aldehydic proton. | |

Figure 3:
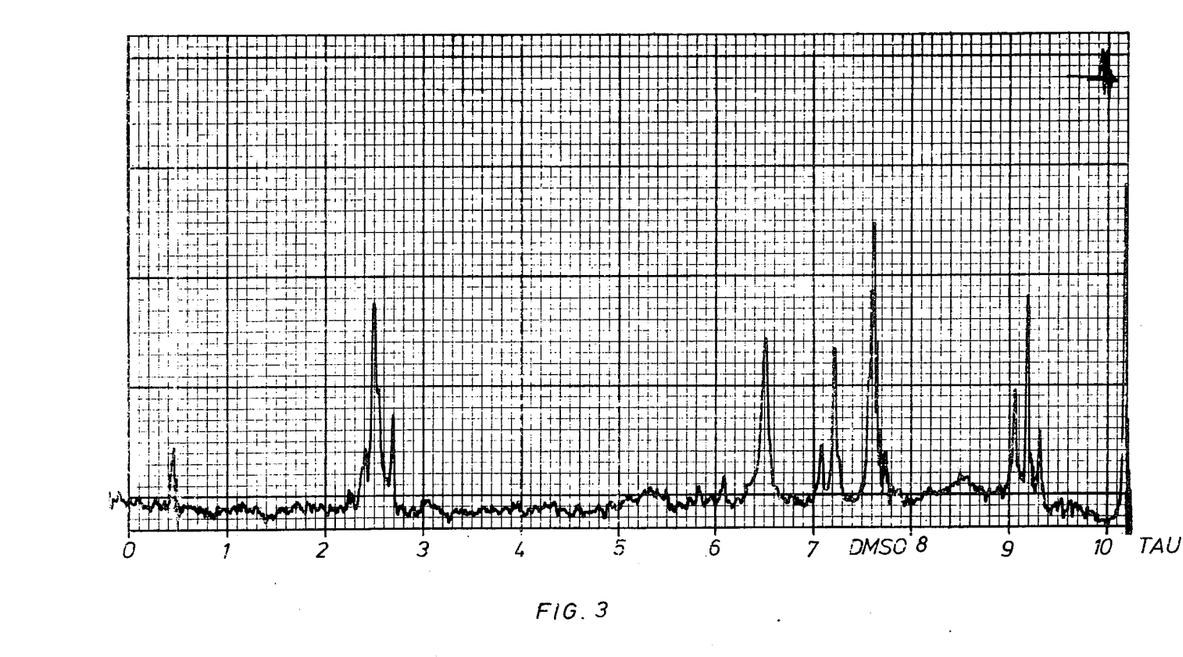

The NMR spectrum after deuteration is shown as FIG. 3 of the drawings and shows that although there are exchangeable protons, as indicated by the additional shift at ($\delta$=3.5 p.p.m.) for example, there is no change in the shift at ($\delta$=9.68 p.p.m.). One of the exchangeable protons may be the proton of the hydrochloride salt.

EXAMPLE 2

The procedure of Example 1 was repeated, using 18 ml of n-butyraldehyde in place of the propionaldehyde. The product was isolated and recrystallized as in Example 1 and there were obtained 2.4 grams of colourless crystals of the n-butyraldehyde adduct of 7-chloro-2-(N-methyl-1-hydroxybutylamino)-5-phenyl-3H-1,4-benzodiazepine-4-oxide hydrochloride (compound V; $R_1$=chlorine in the 7-position, $R_2$=methyl, $R_3$=n-propyl, $R_4$=phenyl) which melted at 193° C with decomposition.

The results of analysis of the product are as follows:

Calculated for $C_{24}H_{31}Cl_2N_3O_3$: C=60.0%; H=6.5%; N=8.8%; Found: C=59.9%; H=6.4%; N=8.8%.

Figure 4:
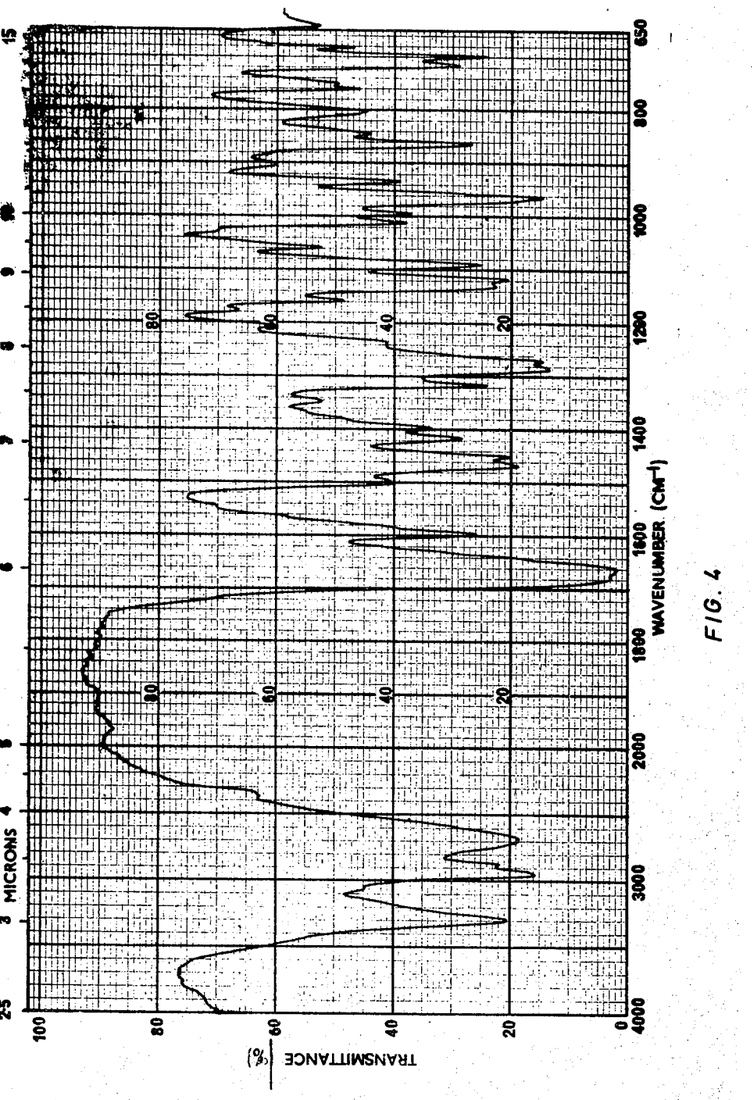
Figure 5:
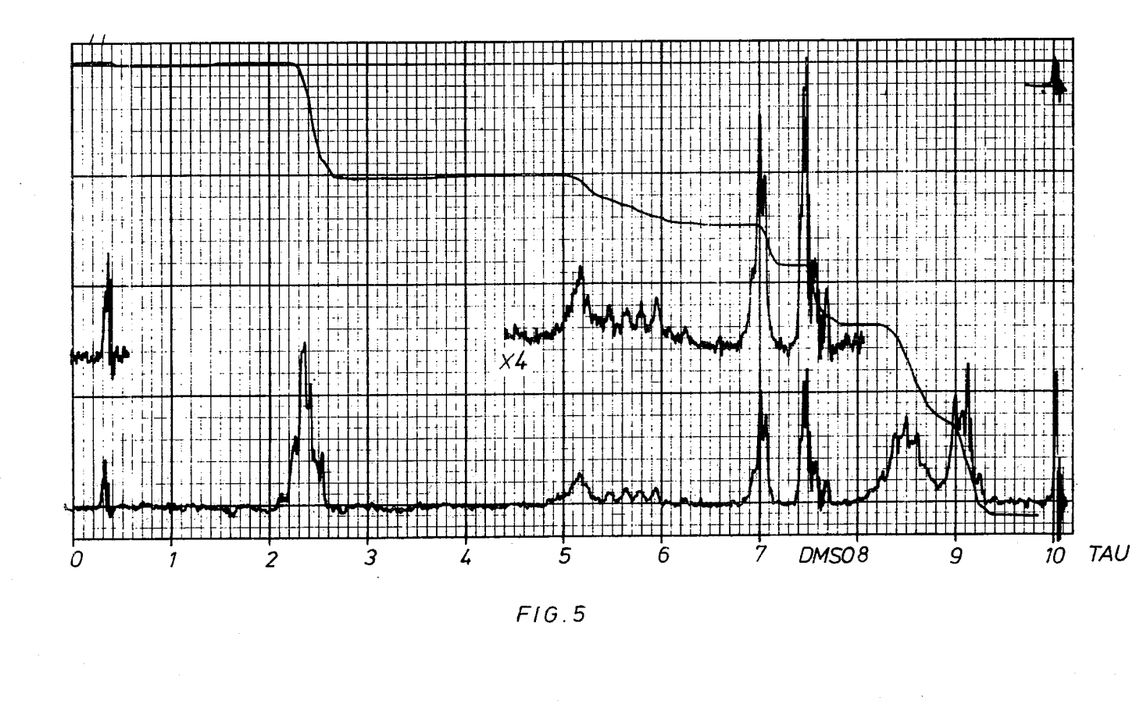

The IR spectrum of the product is shown in FIG. 4 of the drawings and the NMR spectrum is shown in FIG. 5. In the NMR spectrum the following shifts can be assigned to given groups:

| $\delta$(p.p.m.) | | Assignation to: | |
|---|---|---|---|
| 0.76–1 | (complex multiplet) | —$CH_3$ | Two —$CH_2CH_2CH_3$ groups |
| 1.3–1.74 | (complex multiplet) | —$CH_2$— | |
| 2.97 | (doublet) | —N—$CH_3$ | |
| 3.75–4.95 | (complex multiplet) | | |
| 7.46–7.8 | (complex multiplet) | aromatic protons. | |
| 9.68 | (broad singlet) | aldehydic proton; | |

Figure 6:
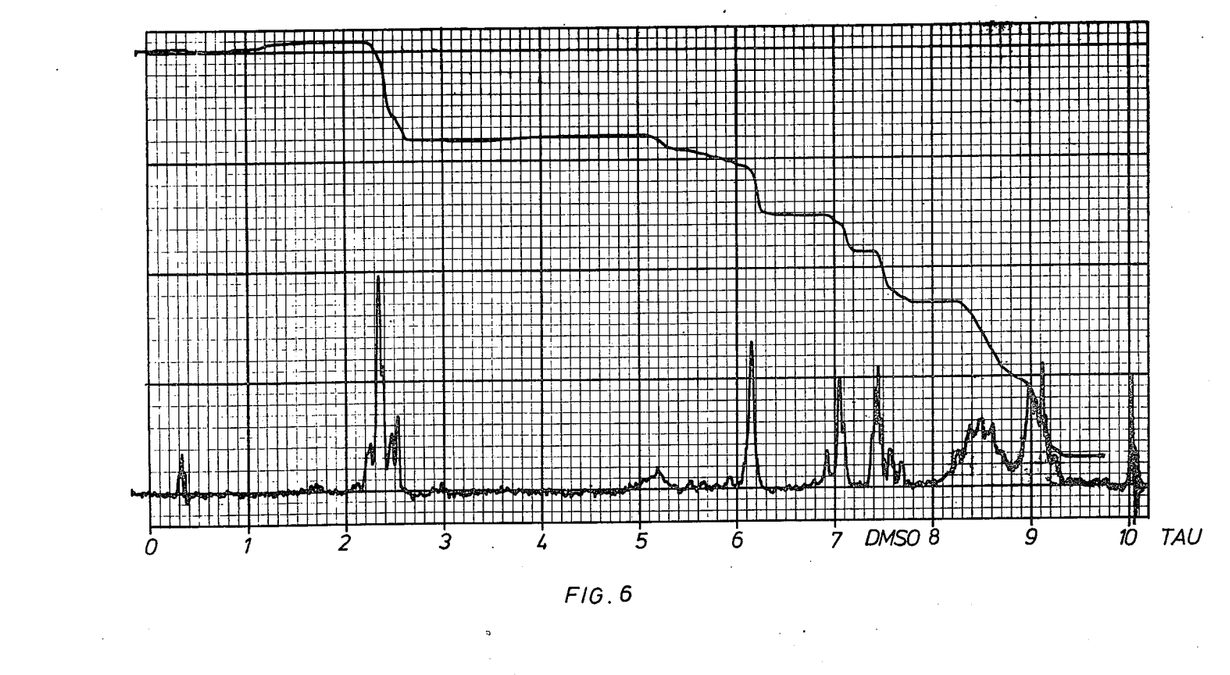

The NMR spectrum after deuteration is shown as FIG. 6 of the drawings and shows that although there are exchangeable protons, as indicated by the additional shift at ($\delta$=3.85 p.p.m.) for example, there is no change on deuteration in the shift at ($\delta = 9.68$ p.p.m.). Exchangeable protons may be the protons of the hydrogen chloride salt and of the hydroxy group.

EXAMPLE 3

The product of Example 1, the n-propionaldehyde adduct of 7-chloro-2-(N-methyl-1-hydroxypropylamino)-5-phenyl-3H-1,4-benzodiazepine-4-oxide hydrochloride, (1 g) was dissolved by refluxing for 5 to 10 minutes with isopropyl alcohol (15 ml) and left at room temperature for two days to evaporate. The crystals which formed were collected and triturated with a mixture of methanol and ether. The yield of 7-chloro-2-(N-methyl-1-hydroxypropylamino)-5-phenyl-3H-1,4-benzodiazepine-4-oxide hydrochloride (compound II; $R_1$ = chlorine in the 7-position; $R_2$ = methyl; $R_3$ = ethyl; $R_4$ = phenyl) was 240 mg. M.P. 192°–4° (with decomposition). The I.R. spectrum was identical to a sample prepared as described in Example 2 of British Pat. Specification No. 1,359,287.

EXAMPLE 4

The product of Example 2, the n-butyraldehyde adduct of 7-chloro-2-(N-methyl-1-hydroxybutylamino)-5-phenyl-3H-1,4-benzodiazepine-4-oxide hydrochloride, (500 mg) was dissolved by refluxing for 5 to 10 minutes with isopropyl alcohol (5 ml) and left at room temperature for two days to evaporate. The gummy residue was triturated with a mixture of methanol and ether. The yield of crystalline product of 7-chloro-2-(N-methyl-1-hydroxybutylamino)-5-phenyl-3H-1,4-benzodiazepine-4-oxide hydrochloride (compound II; $R_1$ = chlorine in the 7-position; $R_2$ = methyl; $R_3$ = n-propyl; $R_4$ = phenyl) was 50 mg, melting at 194° C to 195° C with decomposition. The I.R. spectrum was identical to a sample prepared as described in Example 3 of British Pat. Specification No. 1,359,287.

EXAMPLE 5

40% aqueous sodium hydroxide solution (6 ml) was added to a stirred suspension or solution of the n-propionaldehyde adduct of 7-chloro-2-(N-methyl-1-hydroxypropylamino)-5-phenyl-3H-1,4-benzodiazepine-4-oxide hydrochloride of Example 3 (4.5 g) in methanol (120 ml). The mixture was left standing for 18 hours at room temperature. Crystals that precipitated were filtered and washed with a little methanol followed by water. The yield of pale yellowish crystals of 6-chloro-2-ethyl-9-methyl-4-phenyl-9H-azeto-[2,3-b][1,4]-benzodiazepine (compound III; $R_1$ = chlorine in the 6-position; $R_2$ = methyl; $R_3$ = ethyl; $R_4$ = phenyl) was 2 g, M.P. 194° C to 195° C. This material contains a trace of methanol as solvent of crystallisation.

The results of analysis were as follows:
Calculated for $C_{10}H_{16}ClN_3$: C = 70.9%; H = 5.0%; N = 13.1% Found: C = 70.7%; H = 5.2%; N = 13.0%

EXAMPLE 6

40% aqueous sodium hydroxide solution (6 ml) was added to a stirred solution of the n-butyraldehyde adduct of 7-chloro-2-(N-methyl-1-hydroxybutylamino)-5-phenyl-3H-1,4-benzodiazepine-4-oxide hydrochloride of Example 4 (4.8 g) in methanol (60 ml). The mixture was left standing for 18 hours at room temperature. Crystals that precipitated were filtered and washed with a little methanol followed by water. The yield of needle-like soft crystals of 6-chloro-9-methyl-4-phenyl-2-propyl-9H-azeto-[2,3-b] [1,4]-benzodiazepine (compound III; $R_1$ = chlorine in the 6-position; $R_2$ = methyl; $R_3$ = n-propyl; $R_4$ = phenyl) was 1.5 g, M.P. 179° C to 180° C.

The results of analysis were as follows:
Calculated for $C_{20}H_{18}ClN_3$: C = 71.5%; H = 5.4%; N = 12.5% Found: C = 71.2%; H = 5.4%; N = 12.6%

EXAMPLE 7

The 6-chloro-2-ethyl-9-methyl-4-phenyl-9H-azeto-[2,3-b][1,4] benzodiazepine of Example 5 (322 mg) was treated with a saturated methanolic hydrogen chloride solution (10 ml) and diluted with diethyl ether to obtain colourless crystals. The yield of the hydrochloride salt of 6-chloro-2-ethyl-4-phenyl-9-methyl-9H-azeto-[2,3-b][1,4]-benzodiazepine was 300 mg. The product melted at 189° C to 190° C with decomposition.

EXAMPLE 8

The 6-chloro-9-methyl-4-phenyl-2-propyl-9H-azeto-[2,3-b][1,4]-benzodiazepine of Example 6 (336 mg) was treated with saturated methanolic hydrogen chloride (10 ml) and diluted with ethyl ether to obtain colourless crystals. The yield of the hydrochloride salt of 6-chloro-9-methyl-4-phenyl-2-propyl-9H-azeto-[2,3-b][1,4]-benzodiazepine was 270 mg. The product melted at 183° C to 184° C with decomposition.

What we claim is:

1. A compound of the formula

III wherein $R^1$ represents hydrogen, chlorine, bromine, fluorine, iodine or nitro; $R^2$ represents $C_1$–$C_{10}$ alkyl; $R^3$ represents lower alkyl group and $R^4$ represents phenyl; or a pharmaceutically acceptable acid addition product thereof.

2. A therapeutic composition comprising at least one compound of the formula

III wherein $R^1$ represents hydrogen, chlorine, bromine or nitro; $R^2$ represents methyl or ethyl; $R^3$ represents lower alkyl group and $R^4$ represents phenyl, or a pharmaceutically acceptable acid addition salt thereof in an amount sufficient to provide a tranquilizing, sedative, or hypnotic effect in admixture with a pharmacologically acceptable diluent or carrier.

3. A process for the preparation of a compound according to claim 1 which comprises contacting a compound of the formula wherein $R_1$, $R_2$, $R_3$ and $R_4$ have the significance ascribed in claim 19 to $R^1$, $R^2$, $R^3$ and $R^4$, respectively, with an aqueous solution of a strong base.

4. A process according to claim 3 wherein the base is sodium or potassium hydroxide.

5. 6-chloro-2-ethyl-9-methyl-4-phenyl-9H-azeto-[2,3-b][1,4]-benzodiazepine.

6. 6-chloro-9-methyl-4-phenyl-2-propyl-9H-azeto-[2,3-b][1,4]-benzodiazepine.

7. The hydrochloride salt of 6-chloro-2-ethyl-4-phenyl-9-methyl-9H-azeto-[2,3-b][1,4]-benzodiazepine.

8. The hydrochloride salt of 6-chloro-9-methyl-4-phenyl-2-propyl-9H-azeto-[2,3-b][1,4]-benzodiazepine.

* * * * *

UNITED STATES PATENT AND TRADEMARK OFFICE
CERTIFICATE OF CORRECTION

PATENT NO. : 4,061,745
DATED : December 6, 1977
INVENTOR(S) : UMAKANT DEVDAS SHENOY It is certified that error appears in the above-identified patent and that said Letters Patent are hereby corrected as shown below:

Column 2, line 23, "benzodiazrepine" should read -- benzodiazepine --.

Column 8, line 2, "claim 19" should read -- claim 1 --.

Signed and Sealed this

Twelfth Day of September 1978

[SEAL]

Attest:

RUTH C. MASON
Attesting Officer

DONALD W. BANNER
Commissioner of Patents and Trademarks